United States Patent [19]

Nonobe et al.

[11] Patent Number: 5,618,684

[45] Date of Patent: Apr. 8, 1997

[54] METHOD OF DETERMINATION OF CALCIUM

[75] Inventors: Masatsugu Nonobe, Hyogo-ken; Hozumi Nishida; Tsuyoshi Fujita, both of Osaka-fu, all of Japan

[73] Assignee: Oriental Yeast Co., Ltd., Tokyo, Japan

[21] Appl. No.: 425,972

[22] Filed: Apr. 20, 1995

Related U.S. Application Data

[63] Continuation-in-part of Ser. No. 16,143, Feb. 5, 1993, abandoned.

[30] Foreign Application Priority Data

Feb. 7, 1992 [JP] Japan ........................... 4-56044

[51] Int. Cl.$^6$ .............................. C12Q 1/52; C12Q 1/00; C12Q 1/48; G01N 33/48
[52] U.S. Cl. ................................. 435/16; 435/4; 435/13; 435/15; 435/110; 435/183; 436/63; 436/74; 436/69; 530/300; 530/328
[58] Field of Search ..................... 435/16, 4, 13, 435/15, 110, 183; 436/63, 74, 69; 530/300, 328

[56] References Cited

U.S. PATENT DOCUMENTS

| | | | |
|---|---|---|---|
| 5,015,588 | 5/1991 | Lee et al. | 436/69 |
| 5,049,506 | 9/1991 | Stuber | 436/69 |
| 5,204,240 | 4/1993 | Stuber | 435/13 |
| 5,204,447 | 4/1993 | Bishop et al. | 530/381 |

FOREIGN PATENT DOCUMENTS

| | | |
|---|---|---|
| 59-31698 | 2/1984 | Japan . |
| 61-247963 | 11/1986 | Japan . |
| 0626699 | 1/1987 | Japan . |
| 0626700 | 1/1987 | Japan . |
| 62-36199 | 2/1987 | Japan . |
| 62-036199 | 2/1987 | Japan . |
| 0642598 | 1/1989 | Japan . |
| 64002598 | 1/1989 | Japan . |
| 1231896 | 9/1989 | Japan . |
| 2255098 | 10/1990 | Japan . |

OTHER PUBLICATIONS

Lipmann et al., *A Specific Micromethod for the Determination of Acyl Phosphates*, J. Biol. Chem., vol. 159, No. 21, 1954.

23rd General Meeting of the Association of Japanese Journal of Clinical Laboratory Automation, vol. 16, pp. 222–223, 1991.

Folk et al, *Molecular and Catalytic Properties of Transglutaminases*, Adv. Enzymol., vol. 38, pp. 109–191, 1973.

Hand et al, *Activation of Transglutaminase at Calcium Levels Consistent with a Role for this Enzyme as a Calcium Receptor Protein*, Biological Abstracts, vol. 81, No. 11, 1986.

Muszbek et al, *Kinetic Determination of Blood Coagulation Factor XIII in Plazma*, Clinical Chemistry, vol. 31, No. 1, Jan. 1985, Winston US pp. 35–40.

Klein et al, Jour. of Bacteriology, Apr. 1992, pp. 2599–2605.

*A Referee Method for the Determination of Total Calcium in Serum*, Clinical Chemistry, vol. 19, No. 10, pp. 1208–1213, 1973.

Primary Examiner—John Kight
Assistant Examiner—Louise Leary
Attorney, Agent, or Firm—Browdy and Neimark

[57] ABSTRACT

Calcium in a sample is brought into contact with a transglutaminase capable of being activated with calcium as an activating factor and the transglutaminase activity, which varies depending upon the calcium amount in the sample, is measured to thereby determine the calcium amount in the sample. By the method of the invention, accurate determination of calcium in various samples such as body fluids is possible without removal of proteins from them.

16 Claims, 5 Drawing Sheets

FIG. 5

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Gly  Gly  Gln  Gly
1

METHOD OF DETERMINATION OF CALCIUM

DETAILED EXPLANATION OF THE INVENTION

The present application is a continuation-in-part of the Ser. No. 08/016,143, filed on Feb. 5, 1993 now abandoned, the contents of which are incorporated herein.

FIELD OF THE INVENTION

The present invention relates to a method of determination of calcium and, more precisely, to a method of enzymatic determination of the amount of calcium in which calcium of a sample is brought into contact with an apo-type transglutaminase (EC 2.3.2.13), which does not express the activity in the absence of calcium, thereby to determine the transglutaminase activity, which varies depending upon the amount of the calcium in the sample.

In accordance with the present invention, operation for removal of proteins from a sample is unnecessary and rapid and accurate determination of calcium in a sample is possible. Therefore, determination of calcium in various samples, including live samples such as human serum, is possible by the present invention, which, therefore greatly contributes to, for example, clinical examination and the like.

PRIOR ART AND PROBLEMS THEREOF

In a living body, 99% or more calcium exists locally in bones and teeth thereof, and absorption and excretion of calcium into or from bones are repeated therein in an amount of about 700 mg/day. Therefore, though quantitatively smaller than in bones, calcium exists also in the body fluid and cells. Since calcium in the body fluid and cells participates not only in coagulation of blood but also in other various important actions of live activities, such as neurotransmitting function, myocontracting function and hormone function, the calcium level in the body fluid, especially in blood must be kept strictly constant. As well known, the calcium level in blood is kept constant due to vitamin D, accessory thyroid hormone, calcitonin and the like. In a healthy human body, calcium exists in blood in an amount of from 9 to 11 mg/dl, and the daily variation of the calcium level therein is strictly maintained to be at most +/−3%. However, when a person suffers from a disease, then its calcium level in blood noticeably fluctuates. For instance, the diseases of myxedema, malignant tumor, psychoidosis, hyperproteinemia, hyperthyroidism and the like cause hypercalcemia; while those of hypoparathyroidism, osteomalacia, renal rechitis, uremia, hypoproteinemia, osteotransfer of malignant tumor and the like cause hypocalcemia. Since the blood calcium level in a healthy person is maintained to be constant extremely strictly, even slight fluctuation of the calcium level in a person may be judged to be surely caused by some disease with ease. Therefore, determination of the blood calcium is an extremely important test point for clinical examination.

For determination of the blood calcium, mentioned are an atomic absorption method, an ionic electrode method and a chelate colorimetric method using OCPC (o-cresolphthalein complexon) or the like reagent. However, these methods involve various problems. For instance, an atomic absorption method and an ionic electrode method need complicated operations and particular and expensive instruments; and a chelate colorimetric method needs 8-hydroxyquinoline as a masking reagent since OCPC also reacts on magnesium due to the low reaction specificity thereof. 8-Hydroxyquinoline may mask magnesium to evade the positive error, but it also traps calcium to cause other problems that the coloring sensitivity is lowered and that calcium of a low concentration could not be detected. In addition, the colorimetric method involves another problem that strict and severe control of the reagents to be used is necessary since the degree of coloration of the coloring system extremely varies due to slight fluctuation of the pH value of the system.

Some methods of enzymatic determination of blood calcium are known, using an enzyme like the method of the present invention. For instance, JP-A 62-36199 (the term "JP-A" as used herein means an "unexamined published Japanese patent application") discloses a method of determining calcium in a sample, in which calcium in a sample is reacted with calmodulin to form calcium/calmodulin complex and a calmodulin-dependent enzyme is activated with the resulting complex to measure the enzymatic activity thereof to thereby determine the calcium in the sample. However, the disclosed method involves various problems that dilution of the sample to be tested is necessary since the detectable range is narrow and the sensitivity is high and that the calmodulin and the substrate of the calmodulin-dependent enzyme to be used are expensive and unstable, so that it could hardly apply to various samples of a broad range. JP-A 64-2598 discloses a method of determining calcium in a sample, in which a calcium-containing sample is added to an excess oxalate and the amount of the oxalic acid as precipitated and remained in the reaction system is measured with an oxalic acid oxidase to thereby determine the calcium in the sample. However, the method is not satisfactory, since it needs an operation of precipitating calcium as calcium oxalate, it is influenced by ascorbic acid and bilirubin in the sample as using an oxalic acid oxidase for detection, it gives a standard curve of sloping downwards to the right side, and it cannot be apply to rate assay. JP-A 1-231896 discloses a method of determining calcium in a sample by measuring the enzymatic activity of phospholipase A2 as added to a calcium-containing sample, in which the enzymatic activity varies depending upon the calcium concentration in the sample in the presence of a substrate of a phosphorylcholine thioester. Since the method uses an SH-determining reagent such as DTNB (5,5'-dithiobis-2-nitrobenzoic acid) for detection of the enzymatic activity, it is directly influenced by sulfur-containing compounds such as cysteine and proteins in blood. A calcium determining method of using an amylase has also been reported (Preprints in 23th General Meeting of Association for Promoting Automation of Clinical Examination of Japan, Address Nos. 222 and 223). As well known, however, an amylase also exists in blood and the content thereof largely fluctuates, depending upon the condition of diseases, individuals of themselves and the time. Therefore, when a calcium concentration in a sample is determined on the basis of the amylase activity by the method, then the fluctuation of the blood amylase activity would give any positive or negative error to the calcium determination.

MEANS FOR SOLVING THE PROBLEMS

In consideration of the preceding problems, the present inventors earnestly studied and, as a result, have newly found that a transglutaminase (EC 2.3.2.13) does not exist in blood and has an extremely high specificity to calcium and that the enzymatic activity of an apo-type transglutaminase varies depending upon the amount of calcium as added to the enzyme. On the basis of the findings, they have completed the present invention. Specifically, the present invention relates to enzyme assay of calcium, which is based upon a fundamental technical idea of bringing calcium in a sample into contact with a transglutaminase to measure the transglutaminase activity which varies, depending upon the amount of calcium in the sample, to thereby determine the amount of calcium in the sample.

Precisely, in accordance with the present invention, a sample to be tested is added to a reaction liquid at least containing an apo-type transglutaminase which does not express the activity in the absence of calcium, a substrate and a suitable buffer and detecting reagent so that the apo-type transglutaminase is converted to the corresponding holo-type one in proportion to the calcium amount in the sample, whereupon the enzymatic activity is measured to thereby determine the amount of calcium in the sample.

A transglutaminase has a high specificity to calcium (Adv. Enzymol., 38, 109–191, 1973). Though the enzyme is activated with strontium, as one of other metals than calcium, the km value of itself to strontium is larger than that to calcium by 20 times or more. Strontium is not almost in body samples such as blood or urine. Because of the reasons, the enzyme is said to be highly specific to calcium in clinical examination. Therefore, the present invention is completely free from the problem of magnesium, which is to be taken into consideration in the conventional OCPC method. In addition, a transglutaminase does not exist in serum. Although red corpuscles and platelets contain a blood coagulating factor XIII, which is grouped in the scope of a transglutaminase and which displays the same catalytic action as the enzyme. However, they may be removed from serum in separation of blood clots therefrom. Therefore, the method of the present invention is free from the anxiety about the positive or negative errors which are inevitable in the case of using an amylase. In accordance with the present invention, the transglutaminase activity is calculated from the amount of ammonia or hydroxamic acid to be formed by reaction with a substrate of glutamine peptide or glutamine peptide and amine. Where the activity is determined by detection of ammonia, it is to be noted that a large amount of ammonia is in urine. However, the presence of ammonia in urine causes no problem and determination of calcium in urine may well be effected by the method of the present invention, if a conventional isocitric acid dehydrogenase (ICDH) method (JP-A 61-247963, 62-6700, 62-6699) is applied thereto. Since the amount of ammonia in serum is slight and is therefore negligible. Accordingly, calcium in serum may well be determined by the method of the present invention, to which a conventional glutamic dehydrogenase (GLDH) may be applied. On the other hand, where the activity is determined by detection of hydroxamic acid, the method of the present invention involves no problem. Accordingly, the method of the present invention is superior to any other conventional enzymatic determination methods and is practical to use in daily clinical examinations, since the detection system is hardly influenced by the serum components and the reagents to be used are inexpensive.

In the method of the present invention, blood serum may be subjected directly to calcium measurement without carrying out any pre-treatment such as protein removals i.e., untreated blood serum may be subjected to calcium measurement.

The transglutaminase for use in the present invention may be anyone as extracted and purified from mammalian tissues, vegetables and microorganisms. As a preferred example of it, mentioned is one derived from livers of guinea pigs. For instance, the transglutaminase is obtained by disrupting livers of guinea pigs, subjecting the paste to centrifugation, and thereafter purifying the resulting supernatant by DEAE column chromatography, ammonium sulfate fractionation, gel permeation and hydrophobic chromatography. Preferred is the thus purified one having a high specificity to calcium with a small background. Any specific step is unnecessary for preparation of an apo-type transglutaminase, which may well be effected by merely adding a chelating agent to a buffer to be used in the purification step. If the purified enzyme has a high background, it is to be purified again or it is further subjected to a step of removing calcium therefrom. The morphology of the chelating reagent to be used is not specifically defined. The reagent is preferably one having a large chelating stability constant to calcium (for example, Log KML≧10). Specifically mentioned are EDTA (ethylenediaminetetraacetic acid), CyDTA (trans-1,2-cyclohexanediamine-N,N,N',N'-tetraacetic acid), DTPA (diethylenetriamine-pentaacetic acid), GEDTA (glycol ether diamine-tetraacetic acid), TTHA (triethylenetetramine-hexaacetic acid), methyl EDTA (diaminopropane-tetraacetic acid), etc. The chelating reagent is used in an amount of from 0.01 mM to 1M, preferably from 0.1 mM to 100 mM, in such a way that the transglutaminase is not denaturated by it. The chelating reagent is finally completely removed from the enzyme by dialysis or gel permeation using, for example, Sephadex G-25, so that the enzyme may well be used in the method of the present invention.

The transglutaminase reaction is as shown below.

$$\rightarrow X\text{-}(L\text{-}Glu\text{-}NH\text{-}R)\text{-}Y + NH_3$$

wherein X is an amino acid, peptide or protective group at the N-terminal end L-Gln, Y is an amino acid, peptide or hydrogen atom at the C-terminal end of L-Gln, and R is a compound having at least three carbon atoms or a hydroxyl group. Examples of substrates (donor substrates and acceptor substrates) are presented below.

The substrate to be added to the transglutaminase may be either in the form of a single donor or in the form of combination of a donor and an acceptor. In either case, the enzymatic activity of the transglutaminase is expressed. The transglutaminase has a high specificity to a donor, and various substrates of L-glutamic acid derivatives, tripeptides to higher polypeptides containing L-glutamine, and dipeptide to oligopeptide derivatives containing L-glutamine may be usable. Preferred substrates are benzyloxycarbonyl(Z)-L-Gln-Gly, Z-L-Gln, Z-L-Gln-L-Val, t-butyloxycarbonyl-(Boc)-L-Gln, 9-fluorenylmethoxycarbonyl(Fmoc)-L-Gln, Gly-Gly-L-Gln-Gly (SEQ ID No. 1), etc. On the other hand, since the transglutaminase has a low specificity to an acceptor, amines or hydroxylamines having three or more carbon chains, which are easily available and are inexpensive, are used as an acceptor. Preferably, the substrate for use in the present invention comprises, as a donor, Z-L-Gln-Gly, Z-L-Gln, Boc-L-Gln or Fmoc-L-Gln, and as an acceptor, n-propylamine, n-butylamine, n-amylamine, n-hexylamine, Lys or hydroxylamine. Combination of a donor and an acceptor is preferred to single use of a donor only, as being able to give a larger enzymatic activity in the method of the present invention. Therefore, use of both a donor and an acceptor is recommended in the present invention, as a combined substrate.

For determination of the enzymatic activity in the method of the present invention, X-(L-Glu-NH-R)-Y or $NH_3$ to be formed by the reaction is detected since the transglutaminase catalyzes the preceding reaction. In the process, where a single donor or combination of a donor and an acceptor except hydroxylamine is used as the substrate, $NH_3$ formed is detected. On the other hand, where a combined substrate of a donor and hydroxylamine is used, X-(L-Glu-NHOH)-Y(hydroxamic acid) is detected. For detection of $NH_3$, any and every known method may be employed. As one preferred method, mentioned is a GLDH method. Needless to say, a different ICDH method, which has already been verified effective in various examination centers and which has been modified to have an ammonia-removing system, may also be employed for the purpose. As examples of the method, mentioned are those of using guanidinoacetic acid (JP-A 2-255098), urea (JP-A 61-47963) or creatinine (JP-A 59-31698). Detection of hydroxamic acid may also be effected by any known method. For instance, the method as described in J. Biol. Chem., 159, p. 21 (1954) is employable, in which the property of hydroxamic acid of forming a complex with $Fe^{3+}$ to give a red color is utilized and the absorbance of the complex at 525 nm is measured.

EXAMPLES

The method of the present invention will be explained in more detail by way of the following examples, which, however, are not intended to restrict the scope of the present invention.

Example 1

Reagents

First Reagent

Z-Gln was dissolved in triethanolamine, and L-lysine, reduced glutathione, calcium chloride, α-ketoglutaric acid, ADP, NADH and glutamic dehydrogenase (derived from bovine liver) were added thereto. The resulting mix was adjusted to have pH of 7.5. Distilled water was added thereto to make the concentration of the respective components to be 200 mM, 100 mM, 20 mM, 10 mM, 250 μm, 10 mM, 200 μm, 300 μm and 30 U/ml, respectively. The mix thus prepared is a first reagent.

Second Reagent

Transglutaminase as purified from livers of guinea pigs was diluted with 10 mM tris-acetic acid buffer (pH 7) containing 2 mM of DTT (dithiothreitol) to form an enzyme solution of 10 U/ml.

Samples

Calcium chloride was dissolved and diluted in distilled water to give samples, each having a concentration of 0 mM, 1 mM, 2 mM, 3 mM, 4 mM or 5 mM.

Process

An automatic analyzer of Hitachi 7150 Model was used, in which the first reagent was put in R-1 and the second reagent in R-2. 10 μl of the sample was added to 200 μl of the first reagent and pre-incubated at 37° C. for 5 minutes. Then, 40 μl of the second reagent was added thereto. The reaction system was left as it was for 2 minutes at the same temperature after addition of the second reagent, and the deceleration of the absorbance of the system at 340 nm for one minutes was measured. By detracting the sample blank from the measured value, the result was drawn to give FIG. 1.

Result

Figure 1:
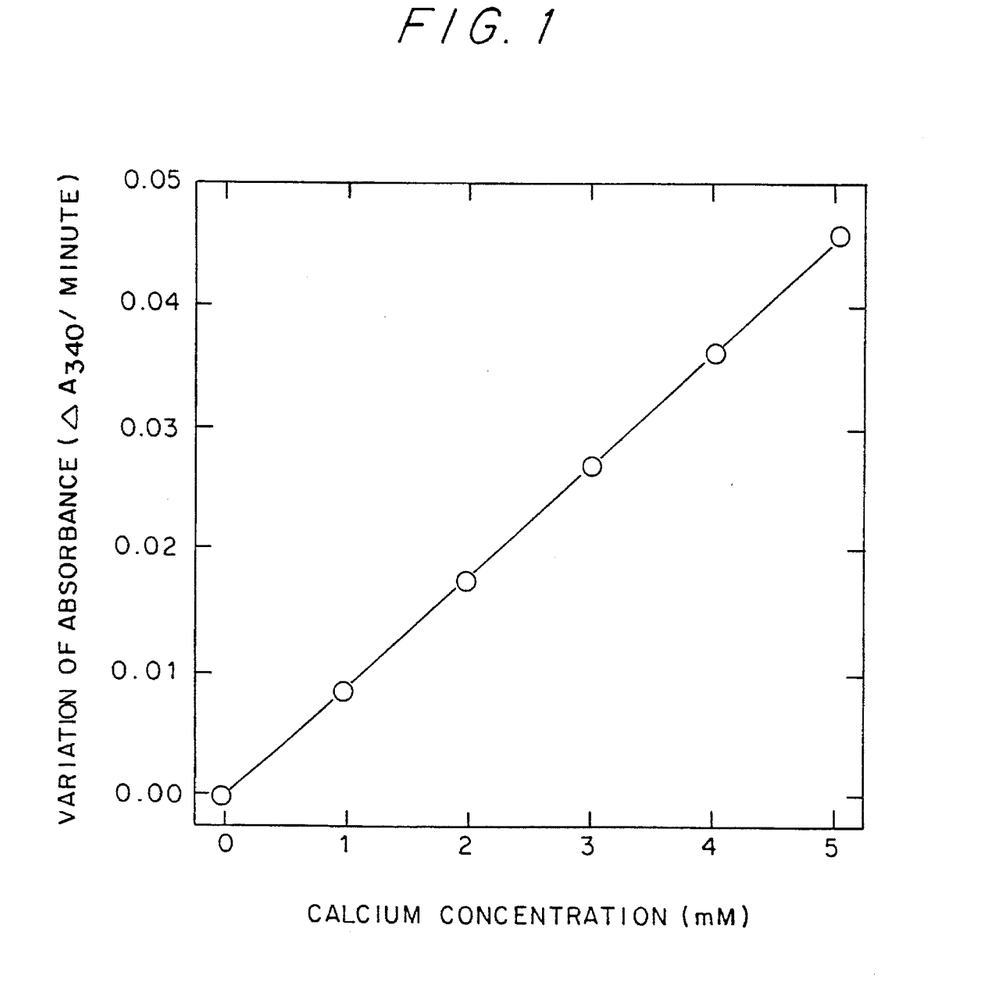
FIG. 1 shows a curve of determining calcium in an NADH system by the method of the present invention.

From the graph of FIG. 1, it is verified that the method of the present invention may determine the amount of calcium in a sample in the form of a linear quantitative determination curve.

Example 2

Reagents

First Reagent

Z-Gln-Gly was dissolved in 1M TRIS solution, and L-lysine, reduced glutathione, calcium chloride, α-ketoglutaric acid, NADH and glutamic dehydrogenase (derived from yeast) were added thereto. The resulting mix was adjusted to have pH of 9 with NaOH. Distilled water was added thereto to make the concentration of the respective components to be 30 mM, 200 mM, 100 mM, 10 mM, 150 μM, 10 mM, 250 μm and 10 U/ml, respectively. The mix thus prepared is a first reagent.

Second Reagent

This is same as that in Example 1.

Samples

These are same as those in Example 1.

Process

This is same as that in Example 1. The result was drawn to give FIG. 2.

Result

Figure 2:
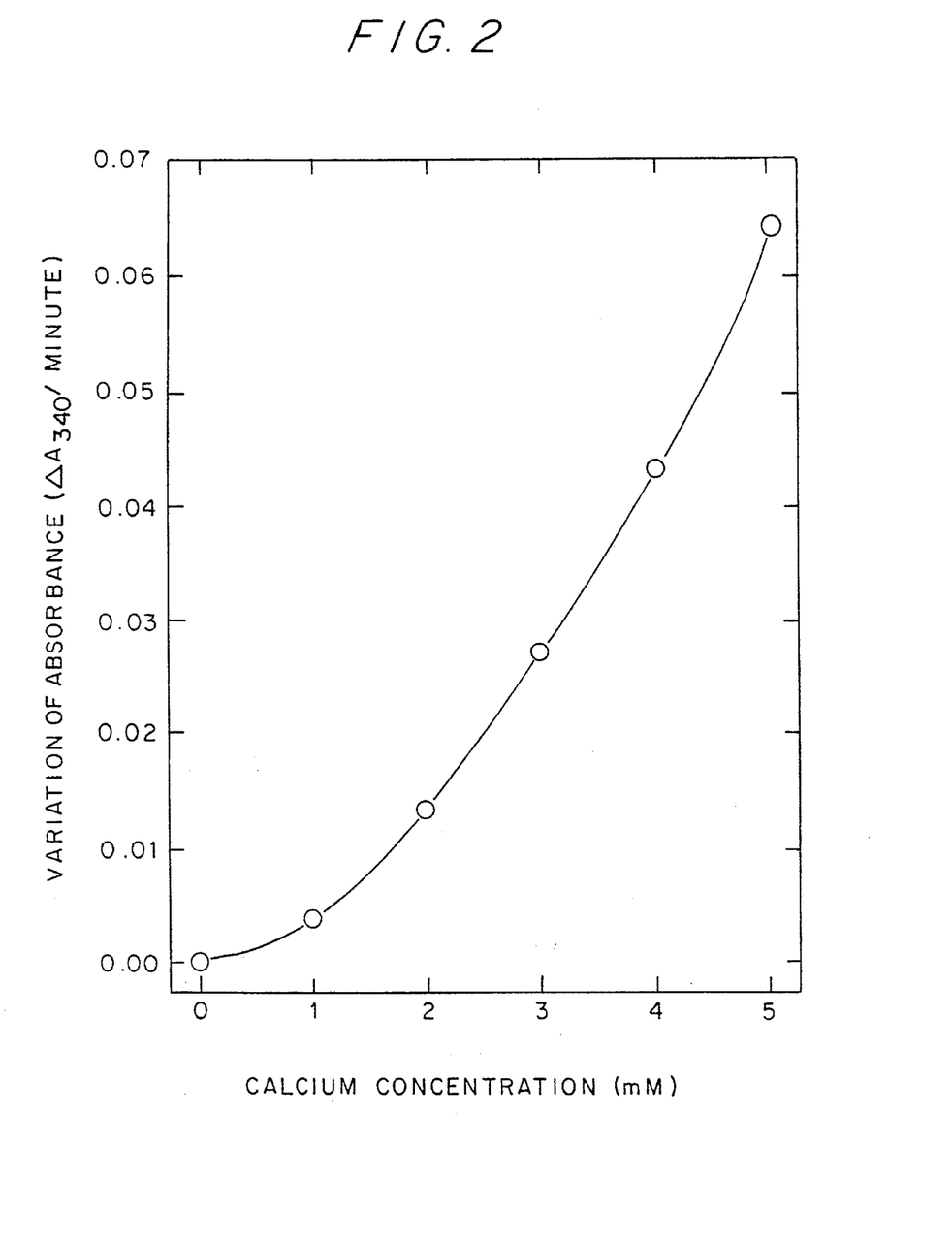
FIG. 2 shows a curve of determining calcium in an NADPH system by the method of the present invention.

As is noted in FIG. 2, the transglutaminase activity in the samples varies, depending upon the calcium concentration in them, in accordance with the method of the present invention. Therefore, it is verified that the calcium concentration in the respective samples is well determined by the method of the present invention.

Example 3

69 samples of human blood serum were subjected to determination of calcium amount in the same manner as in Example 1, directly without removing any ingredients such as protein from said samples of human blood serum.

Each sample was also subjected to determination of calcium amount by an atomic absorption method in the same manner as in CLINICAL CHEMISTRY, Vol. 19, No, 10, P1208–1213, 1973.

Each 0.1 ml of the samples was dissolved into 5 ml of a dilution solution, 0.05 N HCl containing 10 mM LaCl₃, and then subjected to calcium measurment.

Figure 3:
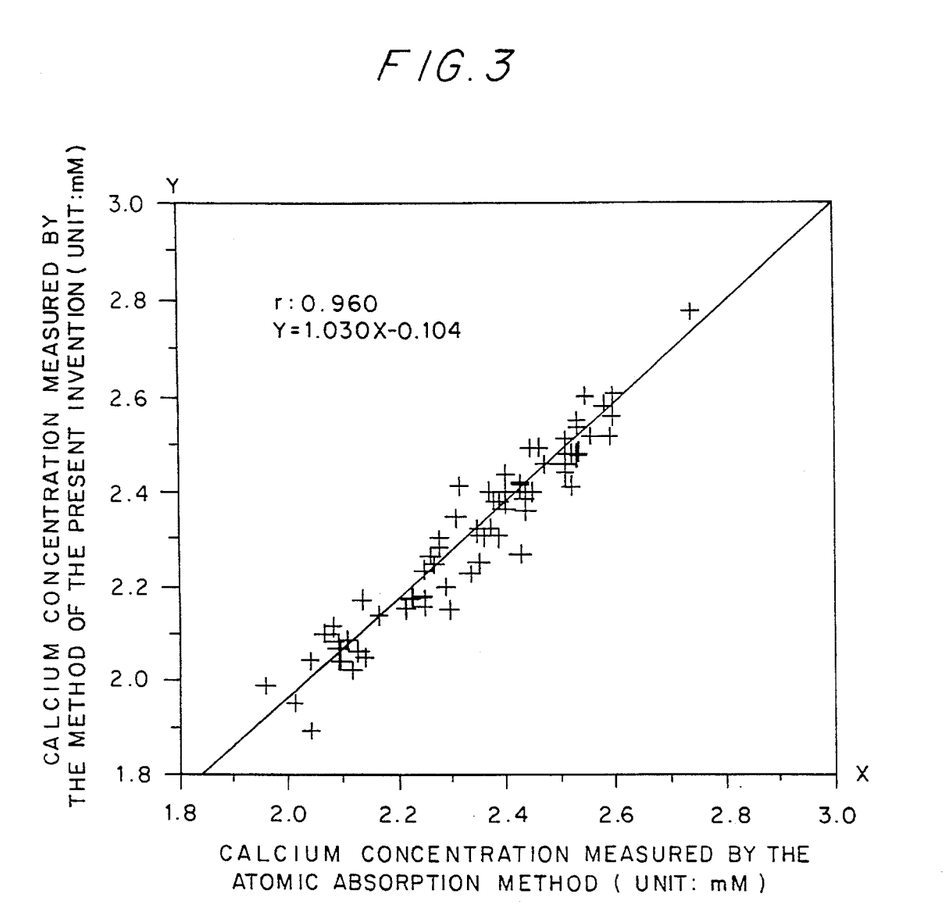
FIG. 3 shows calcium concentration of human blood serum measured by the method of the present invention and by the atomic absorption method.

Comparison of the calcium measurement by the present invention with that by the atomic absorption method is shown in FIG. 3. As seen from FIG. 3, a coefficient of correlation between the data by the method of the present invention and the data by the atomic absorption method is 0.960, namely very high. This shows that the method of the present invention is an excellent method for determination of calcium amount in blood serum.

Example 4

To each 1 ml portion of 200 mM Tris-Acetic acid buffer (pH 6.0) containing 30 mM Z-Gln-gly, 100 mM hydroxylamine hydrochloride, 10 mM reduced glutatione and 2 u/ml transglutaminase, is added 200 µl each of Tris-Acetic acid buffer containing calcium chloride of 0, 0.5, 1.0, 1.5, 2.0, and 2.5 mmol/l, respectively, and then the reaction was carried out at 37° C. for 20 minutes. The reaction was terminated by addition of 1 ml of a solution containing 0.2 mM FeCl₃, 1N HCl and 4% TCA (trichloroacetic acid). After the termination of the reaction, absorbance was measured at 525 nm in a spectrophotometer.

Figure 4:
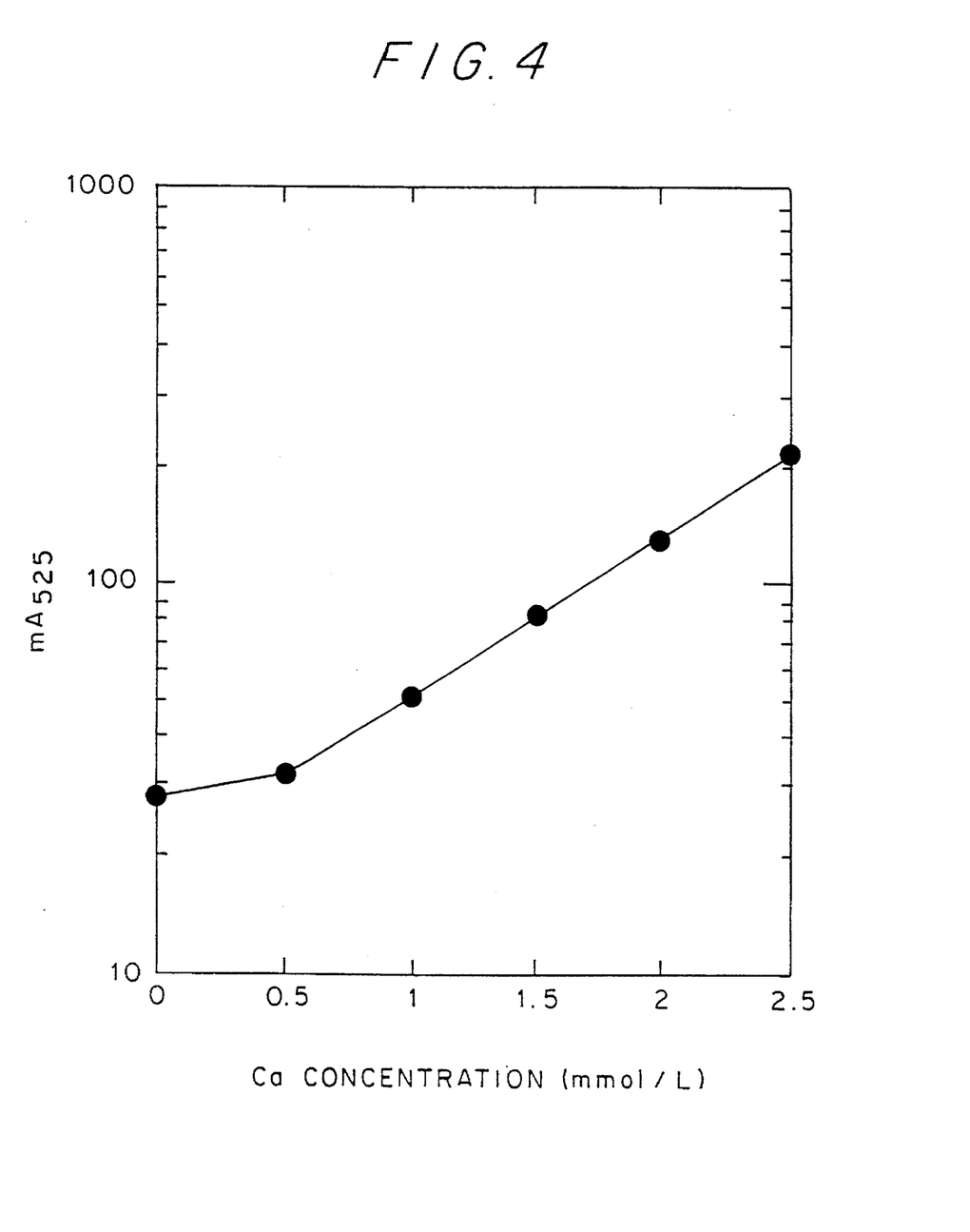
FIG. 4 shows a curve of determining calcium by detection of hydroxamic acid.

As seen from FIG. 4, it is possible to measure calcium concentration of samples, because transglutaminase activity varies depending on calcium concentration.

Example 5

20 samples of human blood serum were subjected directly to calcium measurement, without carrying out any pretreatment, according to the method as in Example 1 and the method as in Example 4 by substituting blood serum samples for solutions of calcium chloride in these Examples; after terminating the reaction by addition of the solution containing 0.2 mM FeCl₃, 1N HCl and 4% TCA as in Example 4, centrifugal separation (10,000 rpm, one min.) was carried out and the obtained supernatants were subjected to the measurement using a spectrophotometer.

The calcium concentration in these blood serum samples were calcumated against FIG. 4 as the standard curve.

Figure 5:
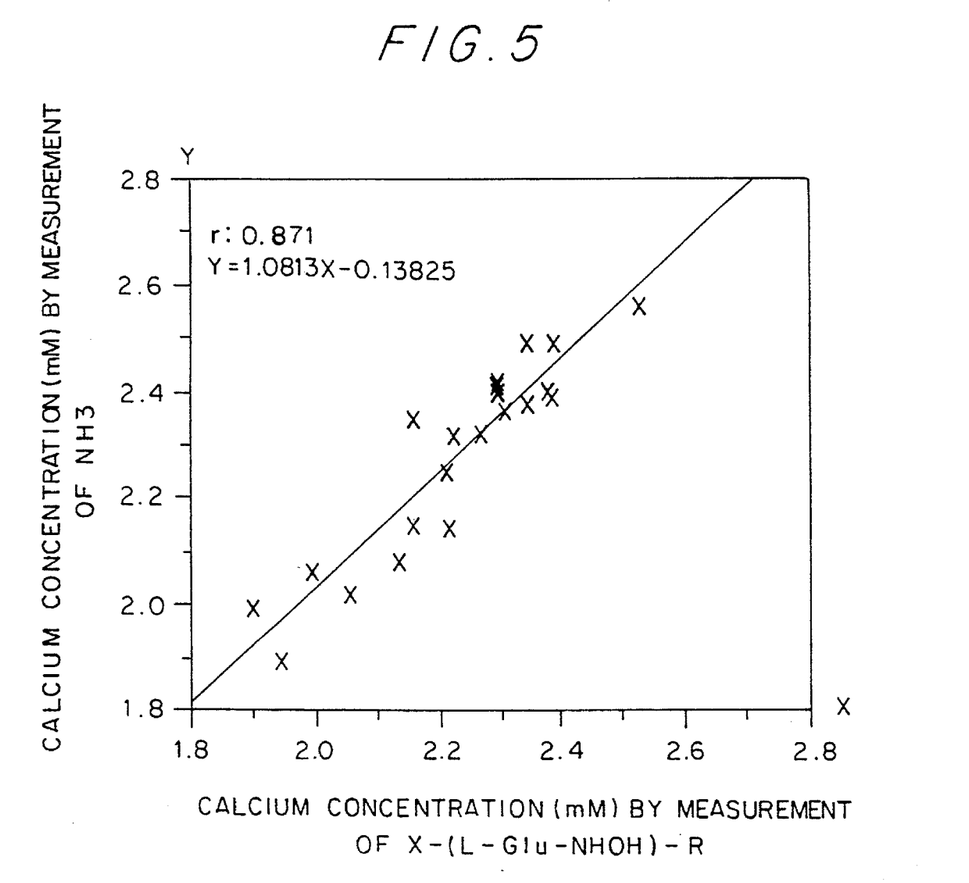
FIG. 5 shows correlation between the data by the method measuring NH$_3$ and the data by the method measuring hydroxamic acid in measurement of blood serum calcium according to the present invention.

As seen from FIG. 5, a coefficient of correlation between the data by the method measuring NH₃ and the data by the method measuring hydroxamic acid, is 0.871, i.e., a high coefficient of correlation.

---

---

We claim:

1. A method of determining the amount of calcium in blood serum, comprising the steps of:

(1) providing a sample of blood serum;

(2) bringing blood serum calcium in said sample of blood serum into contact with a transglutaminase capable of being activated with calcium to provide an activated transglutaminase;

(3) allowing the activated transglutaminase to act on a substrate which is a mixture of a donor and an acceptor to generate NH₃; and (4) measuring the activity of transglutaminase by detecting the amount of NH₃ generated; and (5) determining the amount of calcium in the sample of blood serum by correlating the amount of NH₃ generated with an amount of calcium.

2. A method of determining the amount of calcium in blood serum, comprising the steps of:

(1) providing a sample of blood serum;

(2) bringing blood serum calcium in said sample of blood serum into contact with a transglutaminase capable of being activated with calcium to provide an activated transglutaminase;

(3) allowing the activated transglutaminase to act on a substrate which is a mixture of a donor and an acceptor, wherein said acceptor is hydroxylamine, to generate hydroxamic acid; and (4) measuring the activity of transglutaminase by detecting the amount of hydroxamic acid generated; and (5) determining the amount of calcium in the sample of blood serum by correlating the amount of hydroxamic acid generated with an amount of calcium.

3. A method according to claim 1, wherein said donor is a compound represented by the formula, X-L-Gln-Y, wherein X is an amino acid, peptide or protective group at the N-terminal end of L-Gln, and Y is an amino acid, peptide or hydrogen atom at the C-terminal end of L-Gln, and said acceptor is a compound represented by the formula,

R-NH$_2$, wherein R is $(CH_2)_n CH_3$ where n=2–5, OH or lysine residue (R-NH$_2$=lysine).

4. A method according to claim 2, wherein said donor is a compound represented by the formula, X-L-Gln-Y, wherein X is an amino acid, peptide or protective group at the N-terminal end of L-Gln, and Y is an amino acid, peptide or hydrogen atom at the C-terminal end of L-Gln.

5. A method according to claim 1, wherein said donor is selected from the group consisting of benzyloxycarbonyl-L-Gln-Gly, benzyloxycarbonyl-L-Gln, t-butyloxycarbonyl-L-Gln, and 9-fluorenylmethoxycarbonyl-L-Gln, and said acceptor is selected from the group consisting of n-propylamine, n-butylamine, n-amylamine, n-hexylamine, and lysine.

6. A method according to claim 2, wherein said donor is selected from the group consisting of benzyloxycarbonyl-L-Gln-Gly, benzyloxycarbonyl-L-Gln, t-butyloxycarbonyl-L-Gln, and 9-fluorenylmethoxycarbonyl-L-Gln.

7. A method according to claim 3, wherein said donor is selected from the group consisting of benzyloxycarbonyl-L-Gln-Gly, benzyloxycarbonyl-L-Gln, t-butyloxycarbonyl-L-Gln, and 9-fluorenylmethoxycarbonyl-L-Gln, and the acceptor is selected from the group consisting of n-propylamine, n-butylamine, n-amylamine, n-hexylamine, and lysine.

8. A method according to claim 4, wherein said donor is selected from the group consisting of benzyloxycarbonyl-L-Gln-Gly, benzyloxycarbonyl-L-Gln, t-butyloxycarbonyl-L-Gln, and 9-fluorenylmethoxycarbonyl-L-Gln.

9. A method according to claim 1, further comprising the step of pre-incubating said transglutaminase and said substrate separately at about 37° C. prior to activating said transglutaminase.

10. A method according to claim 1, wherein step (2) is carried out at a temperature of about 37° C. for about two minutes.

11. A method according to claim 9, wherein said transglutaminase is used in said pre-incubation step in an amount of about 10 U/ml.

12. A method according to claim 2, further comprising the step of pre-incubating said transglutaminase and said substrate separately at about 37° C. prior to activating said transglutaminase.

13. A method according to claim 2, wherein step (2) is carried out at a temperature of about 37° C. for two minutes.

14. A method according to claim 12, wherein said transglutaminase is used in said pre-incubation step in an amount of about 10 U/ml.

15. The method according to claim 1, wherein the amount of calcium in the sample of blood serum is determined by calculating from a standard curve the amount of calcium in the sample that corresponds to the amount of NH$_3$ detected as a measure of transglutaminase activity.

16. The method according to claim 2, wherein the amount of calcium in the sample of blood serum is determined by calculating from a standard curve the amount of calcium in the sample that corresponds to the amount of hydroxamic acid detected as a measure of transglutaminase activity.

\* \* \* \* \*